United States Patent [19]

DeWoskin

[11] 4,130,681
[45] Dec. 19, 1978

[54] STRAPPING FOR ORTHODONTIC HEADGEAR AND OTHER USES

[75] Inventor: Irvin S. DeWoskin, St. Louis, Mo.

[73] Assignee: Orthoband Company, Inc., Barnhart, Mo.

[21] Appl. No.: 757,914

[22] Filed: Jan. 10, 1977

[51] Int. Cl.² .................. B32B 3/06; B32B 9/00; A61C 3/00

[52] U.S. Cl. ................... 428/102; 32/14 D; 32/14 B; 428/74; 428/76; 428/123

[58] Field of Search .............. 32/14 B, 14 D; 428/74, 428/102, 121, 76, 103, 104, 123, 224, 279, 302, 425, 480; 2/170, 182.8, 184, 197, 199, DIG. 11, 192

[56] References Cited

U.S. PATENT DOCUMENTS

| 2,742,646 | 4/1956 | Berg | 2/197 |
| 2,874,468 | 2/1959 | DeWoskin | 32/14 D |
| 3,203,099 | 8/1965 | Interlandi | 32/14 D |
| 3,389,043 | 6/1968 | Clark | 428/102 |
| 4,051,555 | 10/1977 | Daly | 2/412 |

Primary Examiner—George F. Lesmes
Assistant Examiner—Daniel R. Zirker
Attorney, Agent, or Firm—Koenig, Senniger, Powers & Leavitt

[57] ABSTRACT

Strapping for orthodontic headgear, wrist watch straps, identificaton straps for hospital use and other uses, comprising a core constituted by a strip of substantially nonstretchable polyester film and a wrapper constituted by a composite strip comprising a layer of polyurethane film and a layer of nonwoven polyester fabric which layers have been bonded together under heat and pressure, the composite strip being wrapped around the side edges of the core with the layer of film on the outside and having its marginal edges overlapped and fused together to form a longitudinal overlap seam by a series of discrete fused stitches, and a method of making the same involving ultrasonic stitching.

6 Claims, 6 Drawing Figures

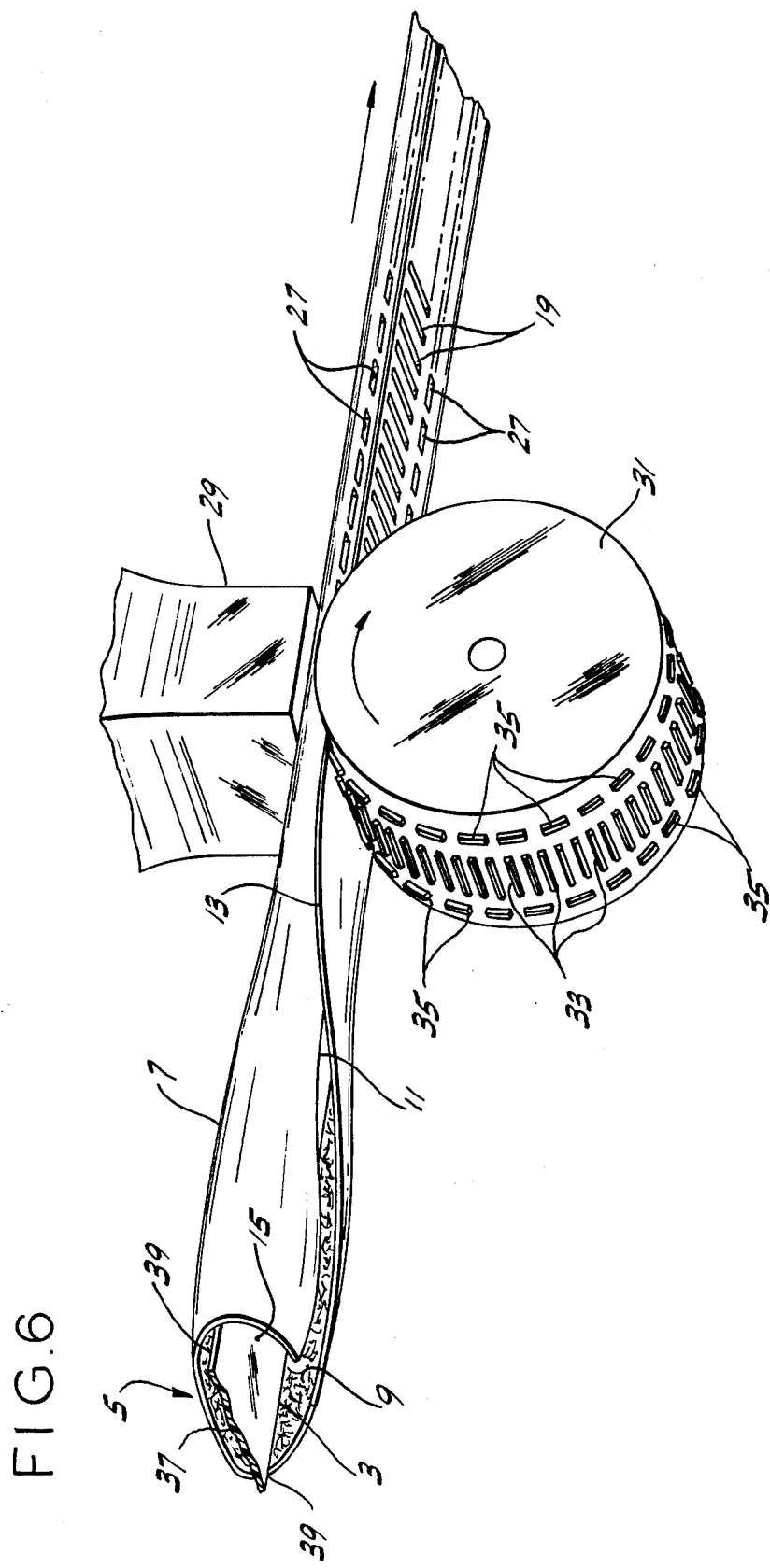

STRAPPING FOR ORTHODONTIC HEADGEAR AND OTHER USES

BACKGROUND OF THE INVENTION

This invention relates to strapping, and more particularly to a composite padded nonstretchable plastic strapping.

While the strapping of this invention is suitable for many and widely varied customary uses of strapping, it has been developed particularly for use as orthodontic headgear strapping (e.g., for orthodontic headgear such as shown in U.S. Pat. Nos. 3,203,099, 3,571,930 and 3,765,093, for example), and is also especially useful for other uses where it comes into contact with the skin, e.g., for wrist watch straps and identification straps for hospital use, or for pet animal collars and harness.

SUMMARY OF THE INVENTION

Among the several objects of the invention may be noted the provision of improved strapping which, while being relatively strong, is relatively lightweight; the provision of such strapping which, while being padded, is generally nonstretchable; the provision of such strapping which is nonallergenic; and the provision of such strapping which is comfortable to wear against the skin.

In general, strapping of this invention comprises a core constituted by a strip of substantially nonstretchable thermoplastic plastic material and a wrapper for the core constituted by a composite strip comprising a layer of thermoplastic film and a layer of thermoplastic padding material bonded to the film, the composite strip being wrapped around the side edges of the core with the layer of film on the outside and the layer of padding material on the inside, and having its marginal edges overlapped on one face of the core along the length of the strapping, said overlapping edges being stitched together to form a longitudinal overlap seam for the composite strip by a series of discrete thermoplastic stitches, said series extending longitudinally of the strip and generally centrally of the strip, said stitches being relatively closely spaced longitudinally of the strapping and penetrating through the strapping from one face thereof to the other, whereby the wrapper is thermoplastically sealed by said stitches to the core at opposite faces of the core as well as being thermoplastically longitudinally seamed.

Other objects and features will be in part apparent and in part pointed out hereinafter.

BRIEF DESCRIPTION OF THE DRAWINGS

FIG. 6 is a perspective illustrating the method of this invention for making the strapping.

Corresponding reference characters indicate corresponding parts throughout the several views of the drawings.

DESCRIPTION OF THE PREFERRED EMBODIMENT

Figure 1:
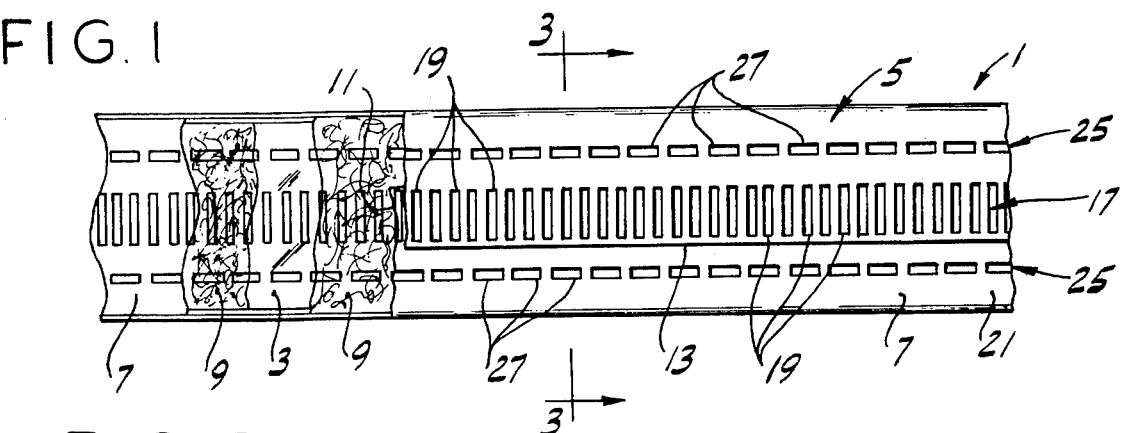
FIG. 1 is a view of one face of a segment of strapping made in accordance with this invention, with layers broken away.
Figure 2:
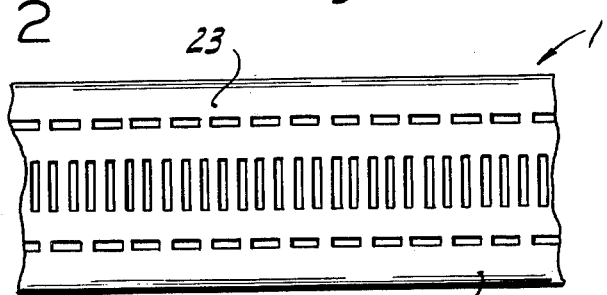
FIG. 2 is a view of the other face of the strapping.

Referring to the drawings, strapping of this invention, designated in its entirety by the reference numeral 1, is shown to comprise a strip 3 of substantially nonstretchable thermoplastic plastic material constituting a core of the strapping and a wrapper 5 for the core 3 constituted by a composite strip comprising a layer of thermoplastic film 7 and a layer of thermoplastic padding material 9 bonded to the film. The core 3 may consist of a strip of polyester film such as that sold under the trade name MYLAR by E. I. duPont De Nemours & Co., or that sold under the trade name FORTREL by Celanese Corporation. It may range from about 2 to about 10 mils in thickness and is preferably about 3 mils thick. In a typical embodiment of the invention, it is about ⅜ inch wide. The composite strip may consist of a layer of polyurethane film such as that sold under the trade name TUFTANE by The B. F. Goodrich Co., which may range from about 1 to about 4 mils in thickness and is preferably about 1½ mils thick, and a layer of random nonwoven polyester fabric such as that sold under the trade name NEXUS by Burlington Mills, these layers having been bonded together face-to-face by heat and pressure.

Figure 3:
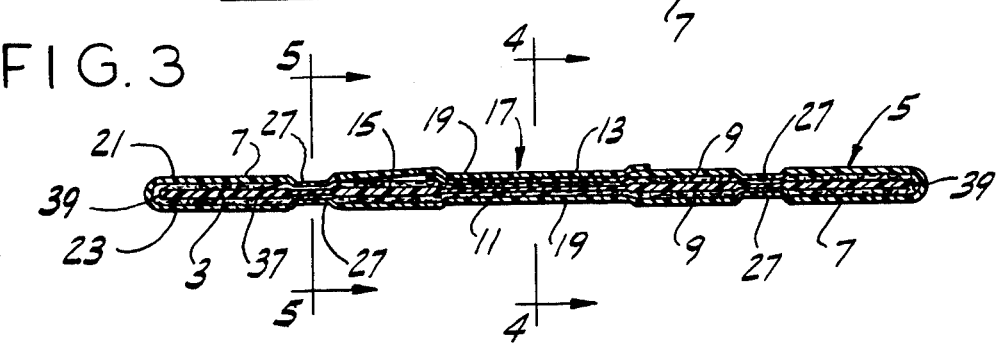
FIG. 3 is an enlarged transverse section of the strapping on line 3—3 of FIG. 1.
Figure 4:
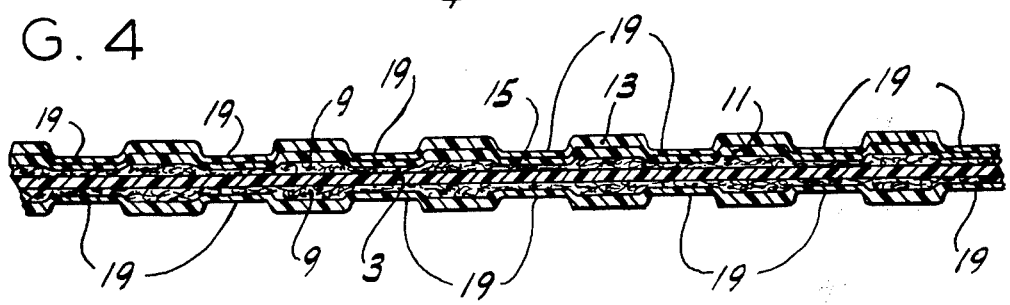
FIGS. 4 and 5 are longitudinal sections of the strapping on lines 4—4 and 5—5, respectively, of FIG. 3.
Figure 5:
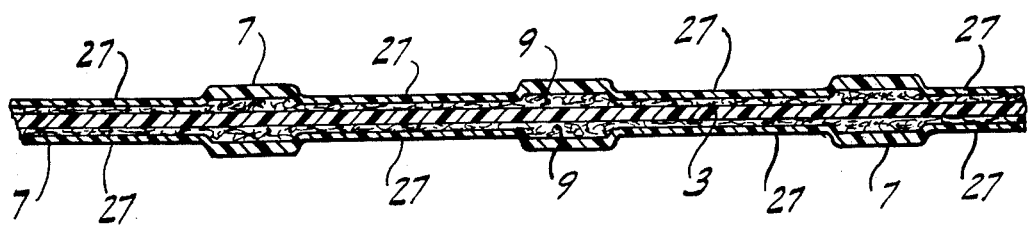

The composite strip 5 is wrapped around the core strip 3 as appears best in FIG. 3 with the polyurethane film layer 7 on the outside and the polyester padding layer 9 on the inside, the marginal edges 11 and 13 of the composite strip 5 being overlapped along one face 15 of the core 3 all along the length of the strapping (this face being the top face of the core strip as viewed in FIG. 3). The width of the composite strip 5 is somewhat greater than twice the width of the core to allow for the overlap of the edges 11 and 13 of the composite strip. Thus, with the core ⅜ inch wide, for example, the composite strip 5 may be 1½ inches wide, providing an overlap of about ¼ inch.

The overlapping edges 11 and 13 of the composite strip (the wrapper) 5 are stitched together to form a longitudinal overlap seam 17 for the composite strip (the wrapper) by a series of discrete thermoplastic stitches 19 (i.e., fused stitches), the series of stitches extending longitudinally of the strip and generally centrally of the strip, and the stitches being relatively closely spaced longitudinally of the strapping and penetrating through the strapping from one face 21 thereof to the other 23, whereby the composite strip (the wrapper) is thermoplastically sealed by the stitches to the core 3 at opposite faces of the core as well as being thermoplastically longitudinally seamed. In a typical embodiment of the invention having a ⅜ inch wide core, and a ¼ inch overlap, the overlap extends generally centrally of the face 15 of the core, and the stitches are elongate fused (and indented) areas about ⅛ inch long and 1/32 inch wide extending transversely of the strapping and spaced about 1/16 inch (center to center).

The composite strip or wrapper 5 is also stitched to the core along lines 25 on opposite sides of the seam 17 by a series of discrete thermoplastic stitches 27 (i.e., fused stitches), each series of stitches 27 extending longitudinally of the strapping with the stitches relatively closely spaced longitudinally of the strapping and penetrating through the strapping from one face thereof to the other. Typically, each stitch 27 is an elongate fused (and indented) area about 1/16 inch long and 1/32 inch wide extending longitudinally of the strapping and spaced about ⅛ inch (center to center).

As shown in FIG. 6, the strapping 1 is made by feeding forward the core strip 3 of polyester film, which is substantially nonstretchable and which is ultrasonically sealable, and simultaneously feeding forward the composite strip or wrapper 5, comprising the layer 7 of polyurethane film and the layer 9 of polyester fabric, both of which are ultrasonically sealable, between the horn 29 and the anvil 31 of an ultrasonic sewing machine, of a type such as shown in U.S. Pat. No. 3,666,599 and sold by Bronson Sonic Power Company of Danbury, Connecticut. The anvil 31 is in the form of a wheel (like the wheel indicated at 24 in U.S. Pat. No. 3,666,599), with a central series of transversely extending ridges 33 all around its periphery for forming the stitches 19, and a pair of series of circumferentially extending ridges 35 all around its periphery on opposite sides of the series of ridges 33 for forming the stitches 27.

The composite strip 5 is combined with the core with the layer 9 of padding material in engagement with the face 37 of the core opposite face 15 of the core, and by folding the margins 11 and 13 of the composite strip at opposite sides of the core around the side edges 39 of the core and overlapping the margins on the face 15 of the core. As the combined strips pass between the horn and the anvil, the overlapping margins 11 and 13 are ultrasonically stitched together along the length of the overlapped margins by the ridges 33, forming the stitches 19 relatively closely spaced longitudinally of the strapping and penetrating through the strapping from one face thereof to the other. Also, the composite strip and the core are ultrasonically stitched together by ridges 35 along the lines 25 on opposite sides of the longitudinal seam 17, these ridges 35 forming the stitches 27. The anvil or wheel 31 rotates in the direction indicated by the arrow in FIG. 6 for feeding the work.

With the substantially nonstretchable core 3, the strapping is relatively strong and nonstretchable, while being of comfortable-to-wear padded construction, via the inclusion of the nonwoven polyester fabric layer 9. The film 7 is per se generally weak and quite stretchable, but the core 3 prevents stretching of the strapping and provides strength. However, the film 7, though weak, is an important element of the strapping in that it is waterproof, stainproof, resistant to abrasion, and non-allergenic, and also functions to prevent fraying of the nonwoven polyester fabric 9. The stitching of the layers, as distinguished from continuous sealing of the layers, is significant in that while providing for securement of the margins 11 and 13 to form the longitudinal seam 17 for the wrapper 5, and securement of the core and the wrapper, it does not break down the layers and develop a tear line, as a continuous seal may do, and it also presents an attractive appearance.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Strapping for orthodontic headgear or other uses comprising a core constituted by a strip of substantially nonstretchable thermoplastic plastic material and a wrapper for the core constituted by a composite strip comprising a layer of thermoplastic film and a layer of thermoplastic padding material bonded to the film, said composite strip being wrapped around the side edges of the core with the layer of film on the outside and the layer of padding material on the inside and having its marginal edges overlapped on one face of the core along the length of the strapping, said overlapping edges being stitched together to form a longitudinal overlap seam for the composite strip by a series of discrete thermoplastic stitches, said series extending longitudinally of the strip and generally centrally of the strip, said stitches being relatively closely spaced longitudinally of the strapping and penetrating through the strapping from one face thereof to the other, whereby the wrapper is thermoplastically sealed by said stitches to the core at opposite faces of the core as well as being thermoplastically longitudinally seamed.

2. Strapping as set forth in claim 1, wherein the composite strip and the core are stitched together on lines extending longitudinally of the strapping on opposite sides of the longitudinal seam by a pair of series of discrete thermoplastic stitches, each of said series extending longitudinally of the strapping with the stitches relatively closely spaced longitudinally of the strapping.

3. Strapping as set forth in claim 1, wherein the stitches are fused elongate areas extending transversely of the strapping.

4. Strapping as set forth in claim 3, wherein the composite strip and the core are stitched together on lines extending longitudinally of the strapping on opposite sides of the longitudinal seam by a pair of series of discrete thermoplastic stitches, each of which is an elongate fused area extending longitudinally of the strapping, and being relatively closely spaced longitudinally of the strapping.

5. Strapping as set forth in claim 1, wherein the film is polyurethane film and the padding material is a nonwoven polyester fabric.

6. Strapping as set forth in claim 5, wherein the core comprises a strip of polyester film.

* * * * *